US00PP07917P

United States Patent [19]

Zaiger et al.

[11] Patent Number: Plant 7,917

[45] Date of Patent: Jul. 21, 1992

[54] APRICOT TREE "JUNECOT"

[76] Inventors: Chris F. Zaiger, 537 Rosemore Ave.; Gary N. Zaiger, 1907 Elm Ave.; Leith M. Gardner, 1207 Grimes Ave.; Grant G. Zaiger, 4005 California Ave., all of Modesto, Calif. 95351

[21] Appl. No.: 644,431

[22] Filed: Jan. 22, 1991

[51] Int. Cl.[5] ..... A01H 5/00

[52] U.S. Cl. ..... Plt./39

[58] Field of Search ..... Plt./39

*Primary Examiner*—James R. Feyrer

[57] ABSTRACT

A new and distinct variety of apricot tree which has the unique combination of outstanding features that are desirable in a new variety:

1. Heavy and regular production of fruit.
2. Fruit with good flavor and eating quality.
3. Fruit with firm flesh, good handling and shipping quality.
4. Large fruit size, relatively uniform throughout the tree.
5. Vigorous semi-spreading growth of tree.
6. Early maturity of the fruit.

1 Drawing Sheet

ORIGIN OF THE VARIETY

Our new and distinct variety of apricot tree was originated by us in our experimental orchard located near Modesto, Calif., as a first generation seedling from a cross between King Apricot (non-patented) and Flaming Gold Apricot (U.S. Plant Pat. No. 2,822). A large number of first generation seedlings were grown and maintained under close observation and the present new variety which evidenced outstanding fruit characteristics was selected for reproduction and commercialization.

ASEXUAL REPRODUCTION OF THE VARIETY

The present new variety of apricot tree was asexually propagated by budding, as performed by us, in our experimental orchard located near Modesto, Calif., and shows that all said characteristics of the tree and its fruit are established and transmitted through succeeding propagations and come true to the original tree.

SUMMARY OF THE VARIETY

The new and distinct variety of apricot tree which is of large size, vigorous, semi-spreading growth and is a heavy and regular bearer of large, firm, yellow flesh, freestone fruit with good flavor and eating quality. The present variety of apricot tree is further characterized as to its novelty by producing fruit that is nearly uniform in size throughout the tree, having good handling and shipping quality and, in comparison to King Apricot (non-patented), having heavier and more regular bearing of fruit and, in comparison to Flaming Gold Apricot (U.S. Plant Pat. No. 2,822), the fruit ripens later by approximately 6 days.

DESCRIPTION OF THE PHOTOGRAPHS

The accompanying color photographic illustrations show typical specimens of the fruit and foliage of the present new apricot variety with the upper and lower surface of the leaves being illustrated and the exterior and sectional view of the fruit divided in its suture plane to reveal flesh coloration, pit cavity and show a stone remaining in place. The photographs were taken shortly after being picked at maturity (firm ripe) and the colors are as nearly true as is reasonably possible in a color representation of this type.

DESCRIPTION OF THE VARIETY

The botanical detailed description of the new and distinct variety of apricot tree, its flowers and fruit are based on observations of specimens grown near Modesto, Calif., with color terminology (except those in common terms) in accordance with Reinhold Color Atlas by A. Kornerup and J. H. Wanscher.

Tree:
- *Size.*—Large.
- *Vigor.*—Vigorous.
- *Growth.*—Semi-spreading.
- *Density.*—Medium dense.
- *Production.*—Productive.
- *Bearer.*—Regular.

Trunk:
- *Size.*—Large.
- *Surface.*—Shaggy.
- *Color.*—Brown to grayish brown (8-E-3) to (8-F-4).

Branches:
- *Size.*—Medium.
- *Surface.*—Medium rough.
- *Lenticels.*—Numerous. Large size.
- *Color.*—Reddish brown on newer growth. Brown to grayish brown on more mature growth.

Leaves:
- *Size.*—Large. Average length — 5". Average width — 3".
- *Form.*—Ovate.
- *Thickness.*—Medium.
- *Texture.*—Smooth.
- *Margin.*—Serrate.
- *Petiole.*—Average length — 1⅜". Average width — 1/16.
- *Glands.*—Size — small. Average number 2, varies from 0 to 4. Globose. Positioned on upper portion of petiole and lower portion of leaf blade.
- *Color.*—Upper surface — green to dark green (27-E-6) to (27-F-6). Lower surface — green to grayish green (27-D-4) to (27-D-6).

Flower buds:

*Size.*—Medium to large.
*Form.*—Plump.
*Length.*—Medium.
*Pubescence.*—Pubescent.

Flowers:
*Blooming period.*—Date of first bloom — Feb. 28, 1990. Date of last bloom — Mar. 6, 1990. Varies slightly due to weather variations.
*Pollen.*—Present.
*Color.*—Pink — fades to white at petal fall.

Fruit:
*Maturity when described.*—Firm ripe.
*Date of first picking.*—May 30, 1990.
*Date of last picking.*—Jun. 6, 1990.
*Size.*—Large. Average diameter axially — 2½". Transverse diameter in suture plane — 2⅜". Average diameter at right angles to suture plane — 2¼".
*Form.*—Nearly globose — slightly elongated. One-half of fruit slightly larger, divided at suture.
*Suture.*—Shallow — extends from stem to apex.
*Ventral surface.*—Nearly rounded, only very slightly lipped.
*Apex.*—Slightly depressed.
*Base.*—Retuse — usually at slight angle from smaller to larger half in suture plane.
*Cavity.*—Rounded to slightly elongated in suture plane. Average depth — ¼". Average breadth — ½".

Skin:
*Thickness.*—Medium.
*Texture.*—Medium — tenacious to flesh.
*Tendency to crack.*—Very slight.
*Down.*—Moderate — very short.
*Color.*—Apricot yellow to yellow orange (5-A-5) to (5-A-7).

Flesh:
*Ripens.*—Evenly.
*Texture.*—Firm.
*Fibers.*—Few, very small, tender.
*Juice.*—Moderate.

*Amydalin.*—Undetected.
*Aroma.*—Moderate.
*Flavor.*—Mild, predominately apricot.
*Eating quality.*—Good.
*Color.*—Light orange to cadmium orange (5-A-6) to (5-A-8). Lighter orange color near pit cavity.

Stone:
*Type.*—Freestone.
*Size.*—Medium. Average length — 1⅛". Average breadth — ⅝". Average thickness — ½".
*Form.*—Ovid.
*Base.*—Usually straight, some rounded.
*Apex.*—Nearly rounded, only very slight pistil point.
*Surface.*—Lightly pitted throughout.
*Ridges.*—Ridges extending across surface of the stone on both sides of suture plane.
*Color.*—Brown to leather brown (5-E-5) to (5-E-6).

Use: Dessert.
*Market.*—Local and long distance.
Keeping quality: Good.
Shipping quality: Good.

The apricot tree and its fruit therein described may vary in slight detail due to cultural practices, soil types and weather conditions under which the variety may be grown; the present description is that of the variety grown under the ecological conditions prevailing near Modesto, Calif.

We claim:

1. A new and distinct variety of apricot tree, as illustrated and described, characterized by its large size, vigorous, semi-dense growth and a protective and regular bearer of firm, yellow flesh, freestone fruit with good flavor and eating quality; the fruit is further characterized by being large in size, nearly uniform throughout the tree, with good storage and shipping quality and the variety is further characterized in comparison to King Apricot (non-patented) by being a more consistent bearer with heavier production of fruit.

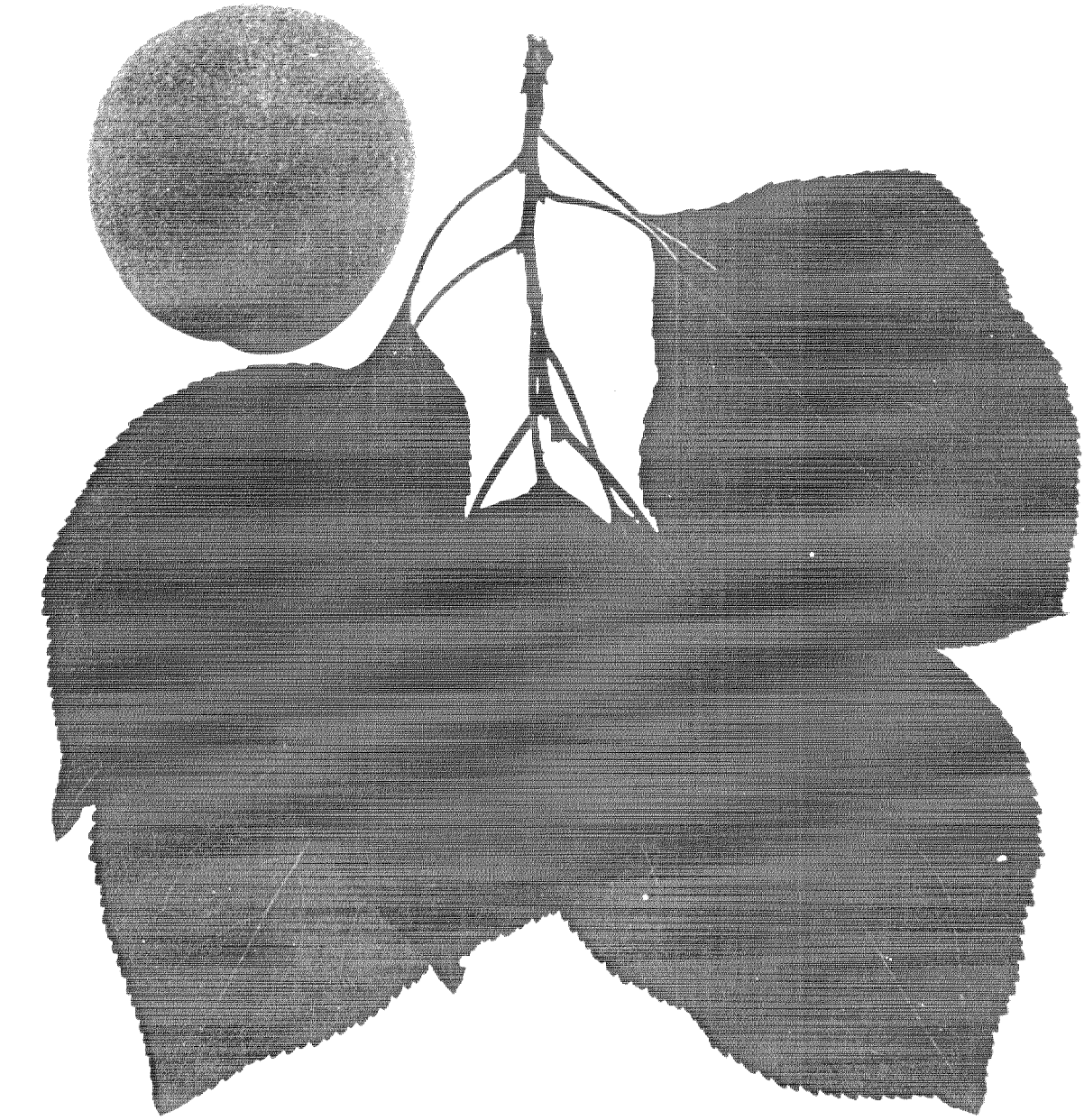
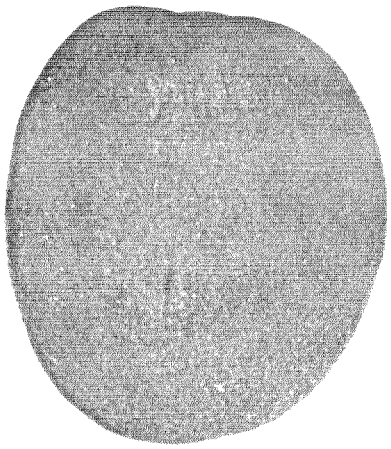
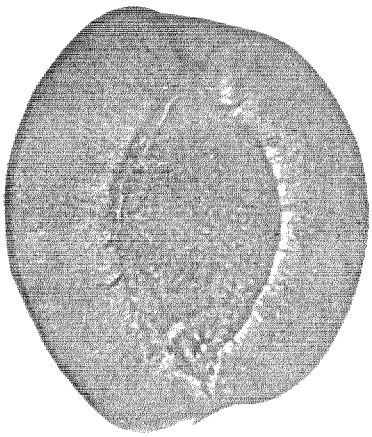
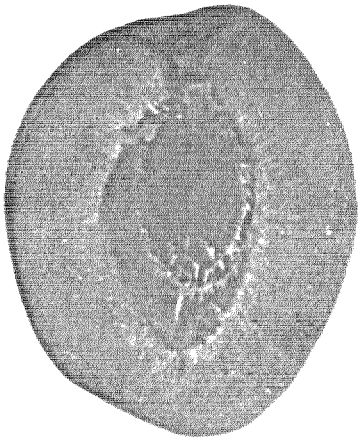

* * * * *